(12) United States Patent
Sendai

(10) Patent No.: US 8,094,778 B2
(45) Date of Patent: Jan. 10, 2012

(54) RADIOGRAPHIC IMAGING DEVICE

(75) Inventor: Tomonari Sendai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/687,898

(22) Filed: Jan. 15, 2010

(65) Prior Publication Data

US 2010/0208865 A1    Aug. 19, 2010

(30) Foreign Application Priority Data

Feb. 16, 2009  (JP) ................................. 2009-032488

(51) Int. Cl.
*A61B 6/02* (2006.01)
(52) U.S. Cl. .......................................... 378/41; 378/114
(58) Field of Classification Search ..................... 378/41, 378/62, 37, 98, 98.2, 98.5, 98.12, 115–116
See application file for complete search history.

(56) References Cited

U.S. PATENT DOCUMENTS

| | | | |
|---|---|---|---|
| 2008/0031411 A1* | 2/2008 | Klingenbeck-Regn | 378/41 |
| 2008/0240336 A1* | 10/2008 | Miyazaki et al. | 378/4 |

FOREIGN PATENT DOCUMENTS

| | | |
|---|---|---|
| JP | 2003-245274 A | 9/2003 |
| JP | 2007-229201 A | 9/2007 |

* cited by examiner

*Primary Examiner* — Hoon Song
(74) *Attorney, Agent, or Firm* — SOLARIS Intellectual Property Group, PLLC

(57) ABSTRACT

There is provided a radiographic imaging device including: a radiation source that irradiates radiation and can move to a directly-facing position at which the radiation source directly faces the object of imaging in a directly-facing direction, a first diagonal incidence position that is at an angle to the directly-facing position, and a second diagonal incidence position that is at an angle at a side opposite the first diagonal incidence position to the directly-facing position; a radiation detector; and a control section that acquires radiologist information relating to an radiologist and, on the basis of the acquired radiologist information, selects one of the first diagonal incidence position and the second diagonal incidence position, wherein the radiographic imaging device captures radiographic images at the directly-facing position and at one of the first diagonal incidence position and the second diagonal incidence position selected by the control section.

4 Claims, 5 Drawing Sheets

REAR    FRONT

RADIOGRAPHIC IMAGING DEVICE

CROSS-REFERENCE TO RELATED APPLICATION

This application is based on and claims priority under 35 USC 119 from Japanese Patent Application No. 2009-032488 filed on Feb. 16, 2009, the disclosure of which is incorporated by reference herein.

BACKGROUND

1. Technical Field

The present invention relates to a radiographic imaging device that captures radiographic images.

2. Related Art

The radiographic imaging devices disclosed in Japanese Patent Applications Laid-Open (JP-A) No. 2003-245274 and No. 2007-229201 are known as radiographic imaging devices.

The radiographic imaging device disclosed in JP-A No. 2003-245274 is structured from a first imaging section that captures a subject of imaging substantially from a front direction and acquires a first image, a second imaging section that captures the subject of imaging from a direction that forms a predetermined angle with respect to the front direction and acquires a second image, and a processing section that processes the first and second images such that they can be used as left and right images for stereo observation.

In the radiographic imaging device disclosed in JP-A No. 2007-229201, an image at an original central position XC (directly-facing position) with respect to an X-ray source 1, and an image at a position (diagonal incidence position) that is moved to the left XL or the right XR, are combined, and a stereoscopic image at various different directions and parallax angles can be observed.

Stereoscopic viewing of images is carried out by visually recognizing one of two images, that have parallax, by the right eye and visually recognizing the other by the left eye.

When stereoscopic viewing is carried out with a directly-facing image that is captured from the front of a subject of imaging and a diagonal incidence image that is captured at an incline with respect to the subject of imaging as in above JP-A Nos. 2003-245274 and 2007-229201, the angles of the images with respect to the subject of imaging are different. Therefore, it is thought that the ease of stereoscopic viewing varies in accordance with which of the directly-facing image or diagonal incidence image the radiologist visually recognizes with the right eye or the left eye.

SUMMARY

In view of the aforementioned, an object of the present invention is to provide a radiographic imaging device that can capture radiographic images that a radiologist can easily view stereoscopically.

A first aspect of the present invention provides a radiographic imaging device including:

a radiation source that irradiates radiation onto an object of imaging, and that can move to a directly-facing position at which the radiation source directly faces the object of imaging in a directly-facing direction, a first diagonal incidence position that is at an angle with respect to the directly-facing position, and a second diagonal incidence position that is at an angle at a side opposite the first diagonal incidence position with respect to the directly-facing position;

a radiation detector that detects radiation that is irradiated from the radiation source and transmitted through the object of imaging, a radiographic image being generated from the detected radiation; and a control section that acquires radiologist information relating to an radiologist, and that, on the basis of the acquired radiologist information, selects one of the first diagonal incidence position and the second diagonal incidence position, wherein the radiographic imaging device captures radiographic images at the directly-facing position and at one of the first diagonal incidence position and the second diagonal incidence position selected by the control section.

In accordance with this structure, the control section acquires radiologist information that relates to an radiologist, and selects one of the first diagonal incidence position and the second diagonal incidence position on the basis of the acquired radiologist information.

The radiation source irradiates radiation onto the subject of imaging at the directly-facing position and at the one of the first diagonal incidence position and the second diagonal incidence position that is selected by the control section.

The radiation detector detects the radiation that is irradiated from the radiation source and transmitted through the object of imaging. A radiographic image is generated from the radiation that the radiation detector detects, and the radiographic image is captured.

In this way, one of the first diagonal incidence position and the second diagonal incidence position is selected on the basis of the radiologist information. Therefore, a capturing position from the direction in which stereoscopic viewing is easy for the radiologist can be selected from among the first diagonal incidence position and the second diagonal incidence position. A radiographic image, that is easy for the radiologist to view stereoscopically, can thereby be captured.

A second aspect of the present invention provides the radiographic imaging device of the first aspect, wherein the control section acquires dominant eye information of the radiologist, and, when the acquired dominant eye information is a right eye, the control section selects one of the first diagonal incidence position and the second diagonal incidence position, and, when the acquired dominant eye information is a left eye, the control section selects another of the first diagonal incidence position and the second diagonal incidence position.

In accordance with this structure, the control section acquires dominant eye information of the radiologist. When the acquired dominant eye information is the right eye, the control section selects one of the first diagonal incidence position and the second diagonal incidence position. When the acquired dominant eye information is the left eye, the control section selects the other of the first diagonal incidence position and the second diagonal incidence position.

Among the both eyes of a person, one eye is the dominant eye. When carrying out stereoscopic viewing, stereoscopic viewing by visually recognizing, with the dominant eye, the image that is captured from the front of the subject of imaging results in a smaller difference between the times when the object is viewed with both eyes and when the object is viewed with a single eye. Therefore, stereoscopic viewing is easy to carry out.

In accordance with the second aspect of the present invention, a radiographic image that is easy for an radiologist to stereoscopically view can be captured regardless of the dominant eye of the radiologist.

A third aspect of the present invention provides the radiographic imaging device of the first and second aspects, wherein a radiation dose that the radiation source irradiates onto the object of imaging is smaller at the first diagonal incidence position and the second diagonal incidence position than at the directly-facing position.

In accordance with this structure, the quality of the image that is captured from the directly-facing direction can be ensured. Image quality can be ensured also at the time of interpreting only the image captured from the directly-facing position, in the same way as in the conventional art.

Because the present invention is structured as described above, radiographic images that an radiologist can easily view stereoscopically can be captured.

BRIEF DESCRIPTION OF THE DRAWINGS

An exemplary embodiment of the present invention will be described in detail based on the following figures, wherein.

DETAILED DESCRIPTION

An example of an exemplary embodiment relating to the present invention will be described hereinafter on the basis of the drawings.
(Structure of Radiographic Imaging Device)

First, the structure of a radiographic imaging device for capturing radiographic images will be described.

A radiographic imaging device 10 relating to the present exemplary embodiment is a device that image-captures, by radiation (e.g., X-rays), a breast N that is an example of a subject of imaging, and is called, for example, a mammography equipment. A radiographic image captured by the radiographic imaging device 10 is displayed by an image display device that will be described later.

Figure 1:
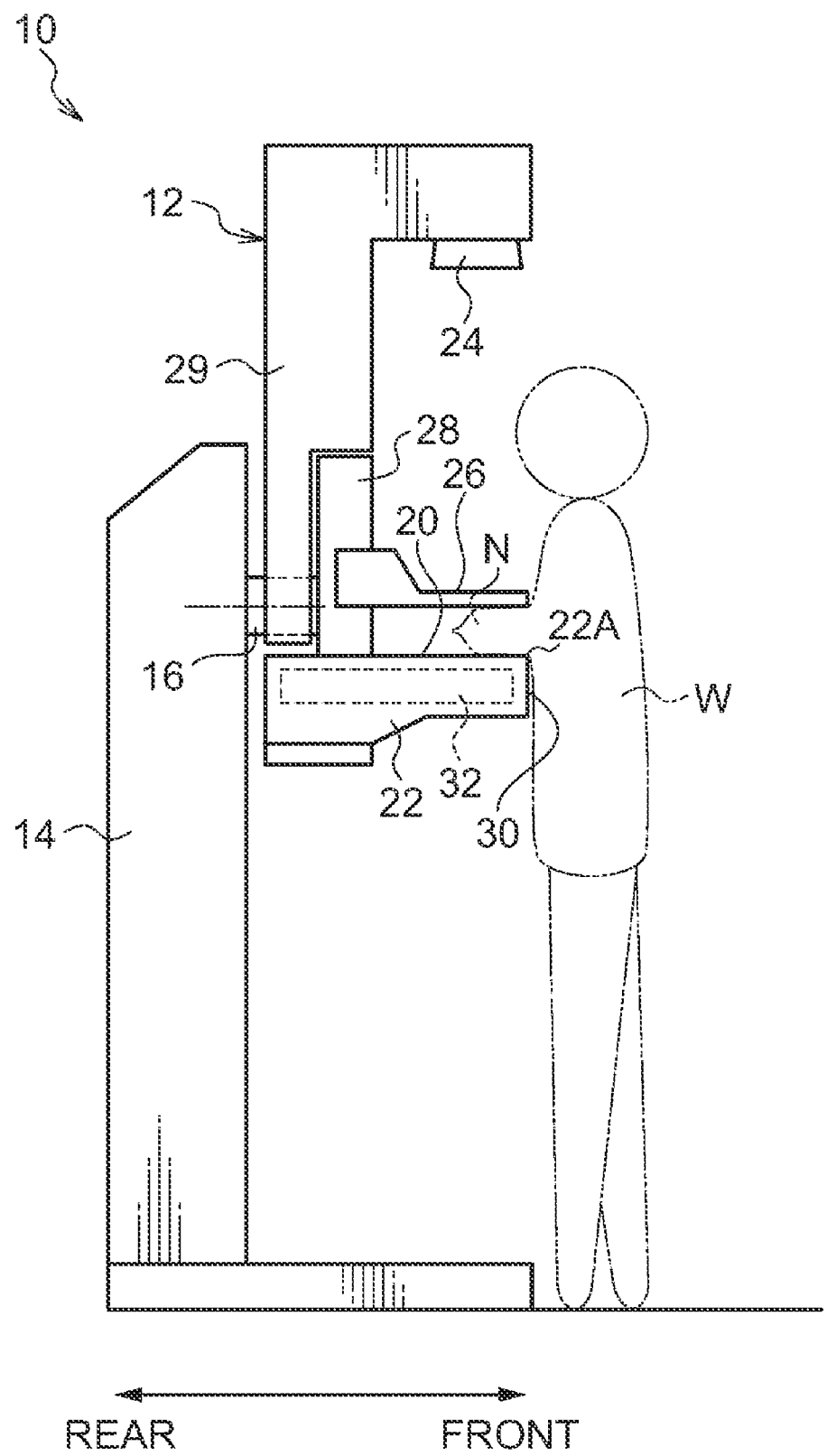
FIG. 1 is a schematic side view showing the structure of a radiographic imaging device relating to an exemplary embodiment.

As shown in FIG. 1, at the radiographic imaging device 10, the breast N of a subject W is image-captured in an erect state in which the subject W is standing. Hereinafter, description will be given with the near side that is close to the subject W who is facing the radiographic imaging device 10 being called the device front side of the radiographic imaging device 10, and the deep side that is far from the subject W who is facing the radiographic imaging device 10 being called the device rear side of the radiographic imaging device 10 (refer to the arrows in FIG. 1). Note that the front and rear of the device are not limited to these.

The object of image capturing at the radiographic imaging device 10 is not limited to the breast N, and may be, for example, another region of the body, or an object. Further, the radiographic imaging device 10 may be a device that image-captures the breast N of the subject W in a seated state when the subject W is seated on a chair or the like. It suffices for the radiographic imaging device 10 to be a device that image-captures the breast N of the subject W with at least the upper half of the body of the subject W being in an erect state.

As shown in FIG. 1, the radiographic imaging device 10 has a measuring section 12 that is substantially shaped as the letter C (the letter U) in side view and that is provided at the device front side, and a base section 14 that supports the measuring section 12 from the device rear side.

Figure 2:
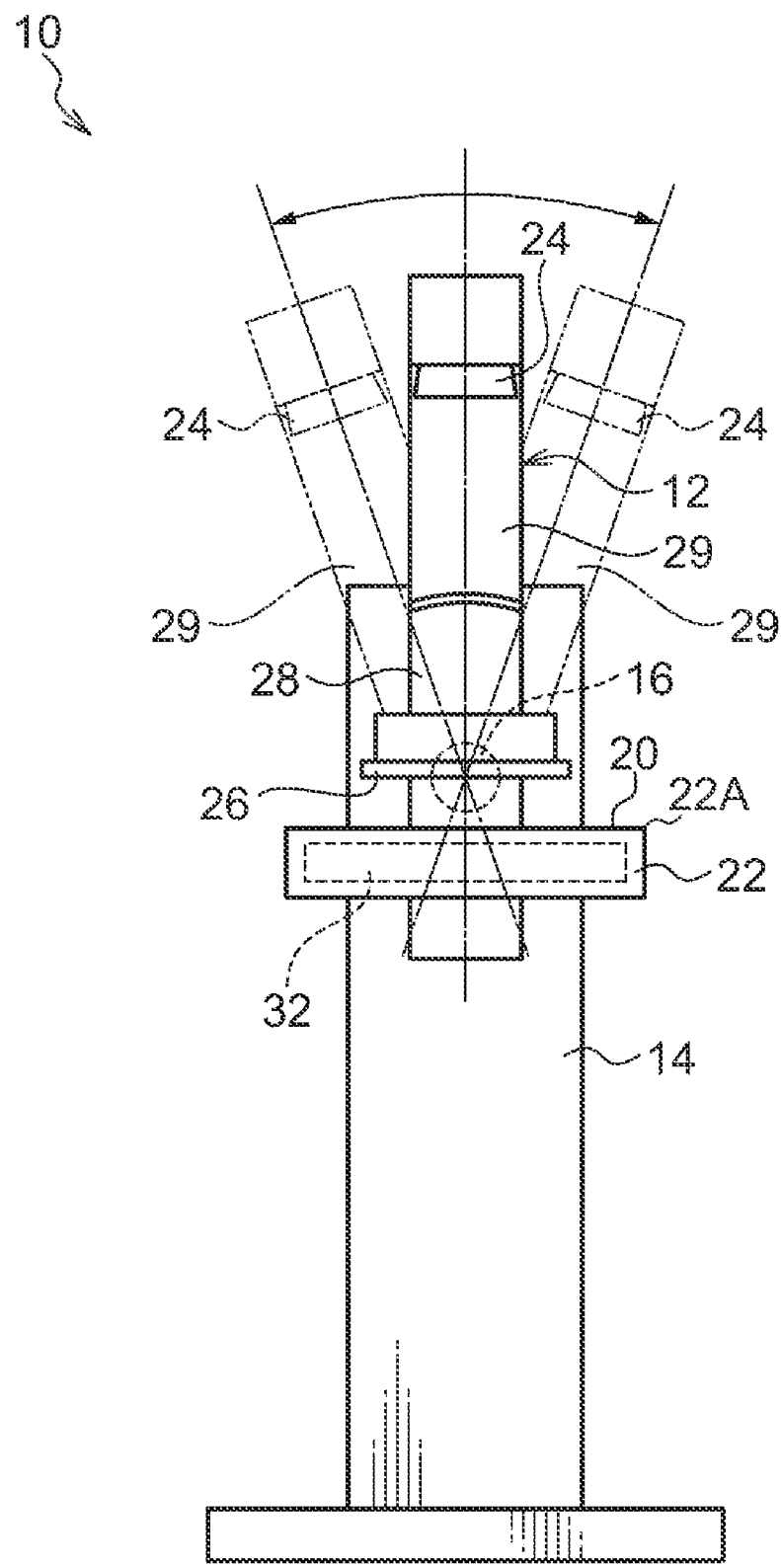
FIG. 2 is a schematic front view showing the structure of the radiographic imaging device relating to the exemplary embodiment.

As shown in FIG. 1 and FIG. 2, the measuring section 12 has an imaging stand 22 at which is formed an imaging surface 20 that is planar and on which the breast N of the subject W who is in an erect state is placed, a compression plate 26 that pushes the breast N against the imaging surface 20, and a holding section 28 that holds the imaging stand 22 and the compression plate 26.

The measuring section 12 has a radiation source 24 that is provided with a X-ray tube (not illustrated) and that irradiates radiation for examination from the X-ray tube toward the imaging surface 20, and a supporting section 29 that is separate from the holding section 28 and supports the radiation source 24.

A rotating shaft 16 that is rotatably supported at the base section 14 is provided at the measuring section 12. The rotating shaft 16 is fixed to the supporting section 29, and the rotating shaft 16 and the supporting section 29 rotate integrally.

The rotating shaft 16 can be switched between a state in which the rotating shaft 16 is connected to the holding section 28 and rotates integrally therewith, and a state in which the rotating shaft 16 is separated from the holding section 28 and rotates idly. Concretely, gears are provided respectively at the rotating shaft 16 and the holding section 28, and the state is switched between a state in which the gears are meshed-together and a state in which the gears are not meshed-together.

Any of various mechanical elements can be used for the switching between transmission/non-transmission of the rotational force of the rotating shaft 16.

The holding section 28 holds the imaging stand 22 and the radiation source 24 such that the imaging surface 20 and the radiation source 24 are separated by a predetermined interval. Further, the holding section 28 slidably holds the compression plate 26 such that the interval between the compression plate 26 and the imaging surface 20 can be varied.

From the standpoints of the radiation transmitting property and strength, the imaging surface 20 that the breast N abuts is formed of carbon for example. A radiation detector 32, on which the radiation that has passed-through the breast N and the imaging surface 20 is irradiated and that detects this radiation, is disposed at the interior of the imaging stand 22. The radiation that the radiation detector 32 detects is made visible, and a radiographic image is generated.

The radiographic imaging device 10 relating to the present exemplary embodiment is a device that can carry out at least both of CC imaging (imaging in the cranial-caudal direction) and MLO imaging (imaging in the mediolateral oblique direction) of the breast N. FIG. 1 and FIG. 2 show the posture of the radiographic imaging device 10 at the time of CC imaging, and FIG. 3 shows the posture of the radiographic imaging device 10 at the time of MLO imaging of the imaging device.

As shown in FIG. 1, at the time of CC imaging, the posture of the holding section 28 is adjusted to a state in which the imaging surface 20 faces upward, and the posture of the supporting section 29 is adjusted to a state in which the radiation source 24 is positioned upward of the imaging surface 20. Due thereto, radiation is irradiated from the radiation source 24 toward the breast N from the head side toward the leg side of the subject W who is in an erect state, and CC imaging (imaging in the cranial-caudal direction) is carried out.

A chest wall surface 30, that is made to abut the chest region that is beneath the breast N of the subject W at the time of CC imaging, is formed at the device front side surface of the imaging stand 22. The chest wall surface 30 is planar.

Figure 3:
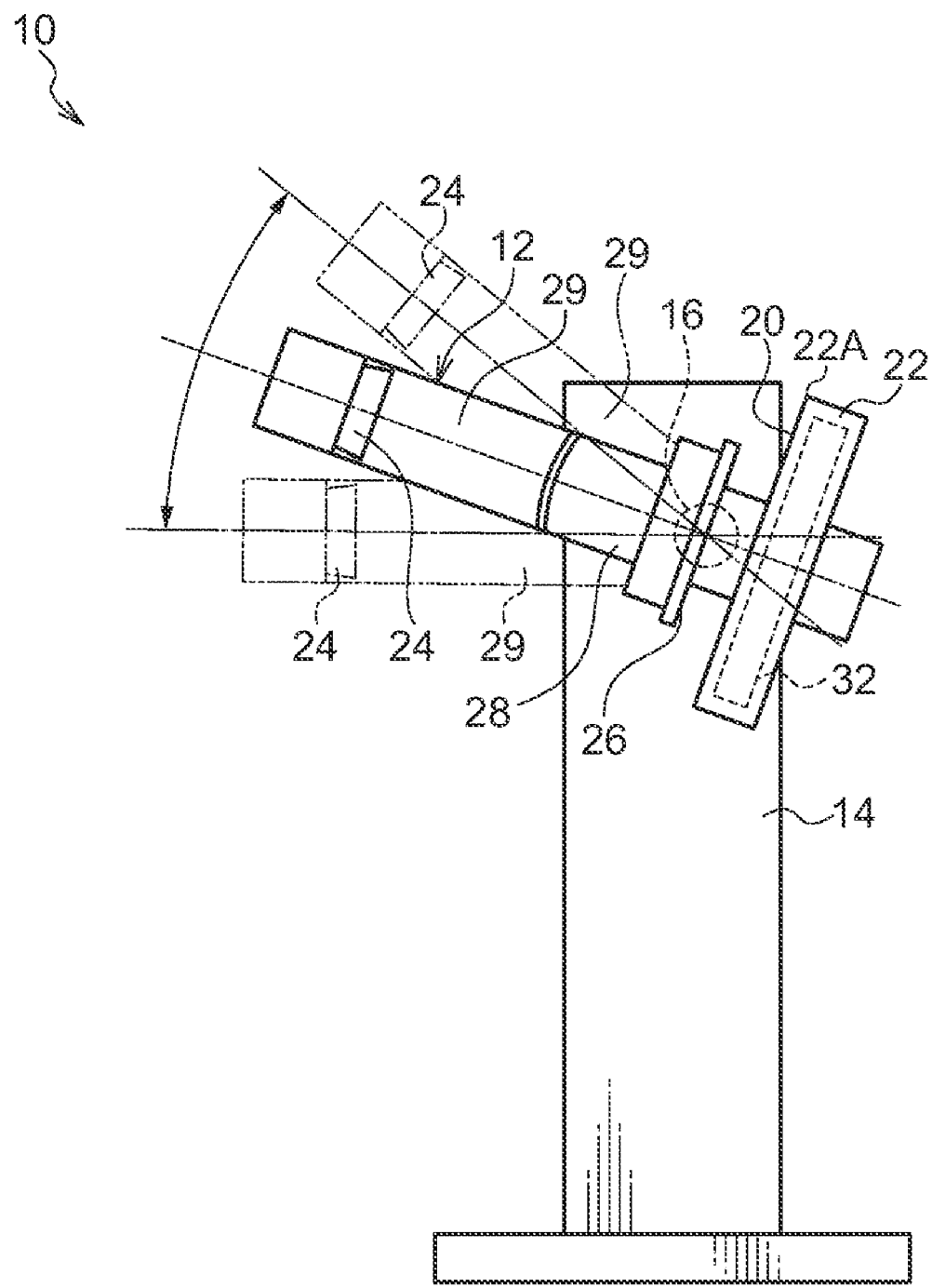
FIG. 3 is a schematic front view showing the structure of the radiographic imaging device at the time of MLO imaging.

At the time of MLO imaging, as shown in FIG. 3, generally, the posture of the holding section 28 is adjusted to a state in which the imaging stand 22 is rotated by greater than or equal to 45° and less than 90° as compared with at the time of CC imaging, and is positioned such that the axilla of the subject W abuts a side wall corner portion 22A at the device front side of the imaging stand 22. Due thereto, radiation is irradiated from the radiation source 24 toward the breast N from the axially central side toward the outer side of the torso of the subject W, and MLO imaging (imaging in the mediolateral oblique direction) is carried out.

Here, at the radiographic imaging device 10, the radiation source 24 can move to a directly-facing position C at which the radiation source 24 directly-faces the breast N in the directly-facing direction, a first diagonal incidence position S1 that is at an angle with respect to the directly-facing direction, and a second diagonal incidence position S2 that is at an angle at the side opposite the first diagonal incidence position S1 with respect to the directly-facing direction.

Specifically, as shown in FIG. 2, the rotating shaft 16 rotates idly with respect to the holding section 28, and the imaging stand 22 and the compression plate 26 do not move, and, due to the supporting section 29 rotating, only the radiation source 24 moves in the form of an arc to the directly-facing position C, the first diagonal incidence position S1 and the second diagonal incidence position S2.

In the present exemplary embodiment, the directly-facing direction is a direction perpendicular to the imaging surface 20. Note that the directly-facing direction may be not a direction that is perpendicular to the imaging surface 20.

The first diagonal incidence position S1 is at an angle of, for example, around 3° with respect to the directly-facing direction. The second diagonal incidence position S2 is at an angle of, for example, around −3° with respect to the directly-facing direction. The first diagonal incidence position S1 is at an angle of around 6° with respect to the second diagonal incidence position S2. Note that the angles of the first diagonal incidence position S1 and the second diagonal incidence position S2 with respect to the directly-facing direction are not limited to the aforementioned angles, and it suffices for them to be angles by which the parallax needed for stereoscopic viewing arises.

When capturing a radiographic image, for example, the radiation source 24 is positioned at the directly-facing position C in the initial state and carries out imaging at the directly-facing position C, and is moved to either of the first diagonal incidence position S1 and the second diagonal incidence position S2 and carries out imaging. Both at the time of CC imaging and at the time of MLO imaging, imaging is carried out at the directly-facing position C and at one of the first diagonal incidence position S1 and the second diagonal incidence position S2, such that two images are captured at each of the time of CC imaging and the time of MLO imaging.

For example, when it is assumed that the radiographic images of the breast N will be displayed in a state in which the nipple is facing upward (see FIG. 4), if capturing the images at the directly-facing position C and the first diagonal incidence position S1, stereoscopic viewing is carried out by the image of the directly-facing position C being visually recognized by the right eye and the image captured at the first diagonal incidence position S1 being visually recognized by the left eye. Further, if images are captured at the directly-facing position C and the second diagonal incidence position S2, stereoscopic viewing is carried out by the image of the directly-facing position C being visually recognized by the left eye and the image captured at the second diagonal incidence position S2 being visually recognized by the right eye.

Further, the radiographic imaging device 10 has a control section 38 that acquires radiologist information relating to the radiologist, and, on the basis of the acquired radiologist information, selects one of the first diagonal incidence position S1 and the second diagonal incidence position S2.

The control section 38 drives and controls a driving section 36, and causes the radiation source 24 to be moved to the selected one of the first diagonal incidence position S1 and second diagonal incidence position S2.

An operation panel 40, that serves as an input section at which inputting operations from the exterior are possible, is connected to the control section 38. Inputted information, that relates to the person carrying out the imaging operation and that is inputted from the operation panel 40, is acquired by the control section 38. Examples of the inputted information relating to the person carrying out the imaging operation include the dominant eye, the visual acuity and the like of the radiologist.

On the basis of the inputted information of the person carrying out the imaging operation, the control section 38 selects one of the first diagonal incidence position S1 and the second diagonal incidence position S2, decides upon the position to which the radiation source 24 is to be moved, and moves the radiation source 24.

Here, the first diagonal incidence position S1 and the second diagonal incidence position S2 are selected in accordance with by which of visual recognition by the right eye and visual recognition by the left eye it would be easier to stereoscopically view the image captured at the directly-facing position C. Namely, if radiographic images of the breast N are to be displayed in a state in which the nipple faces upward (see FIG. 4), the first diagonal incidence position S1 is selected when visual recognition of the image of the directly-facing position C with the right eye is easier for stereoscopic viewing, and the second diagonal incidence position S2 is selected when visual recognition of the image of the directly-facing position C with the left eye is easier for stereoscopic viewing.

Note that, when displaying the radiographic images of the breast N in a state in which the nipple is facing downward, the second diagonal incidence position S2 is selected when visual recognition of the image of the directly-facing position C by the right eye is easier for stereoscopic viewing, and the first diagonal incidence position S1 is selected when visual recognition of the image of the directly-facing position C by the left eye is easier for stereoscopic viewing.

Stereoscopic viewing is easy to carry out because stereoscopic viewing by, for example, visually recognizing, by the dominant eye, the image that is captured from the front of the subject of imaging results in a smaller difference between viewing the object with both eyes and viewing the object with a single eye.

Accordingly, for example, when the control section 38 acquires dominant eye information that expresses that the right eye is the dominant eye, the control unit 38 selects the first diagonal incidence position S1 and moves the radiation source 24 to the first diagonal incidence position S1. Due thereto, capturing of radiographic images is carried out at the directly-facing position C and the first diagonal incidence position S1.

If the control section 38 acquires dominant eye information that expresses that the left eye is the dominant eye, the control unit 38 selects the second diagonal incidence position S2 and moves the radiation source 24 to the second diagonal incidence position S2. Due thereto, capturing of radiographic images is carried out at the directly-facing position C and the second diagonal incidence position S2.

The control section 38 also controls the radiation dose of the radiation source 24. The radiation dose at the first diagonal incidence position S1 and the second diagonal incidence position S2 are made to be smaller than the radiation dose at the directly-facing position C.

By making the amount of radiation from the directly-facing direction be large, the quality of the image that is captured at the directly-facing direction, that is imaging that is the same as in usual mammography, is ensured. Due thereto, image quality is ensured at the time of interpreting the image captured from the directly-facing position C in the same way as in the conventional art, and therefore, the image can be easily read and compared with a usual mammographic image.

(Structure of Image Display Device)

The structure of an image display device will be described next.

Figure 4:
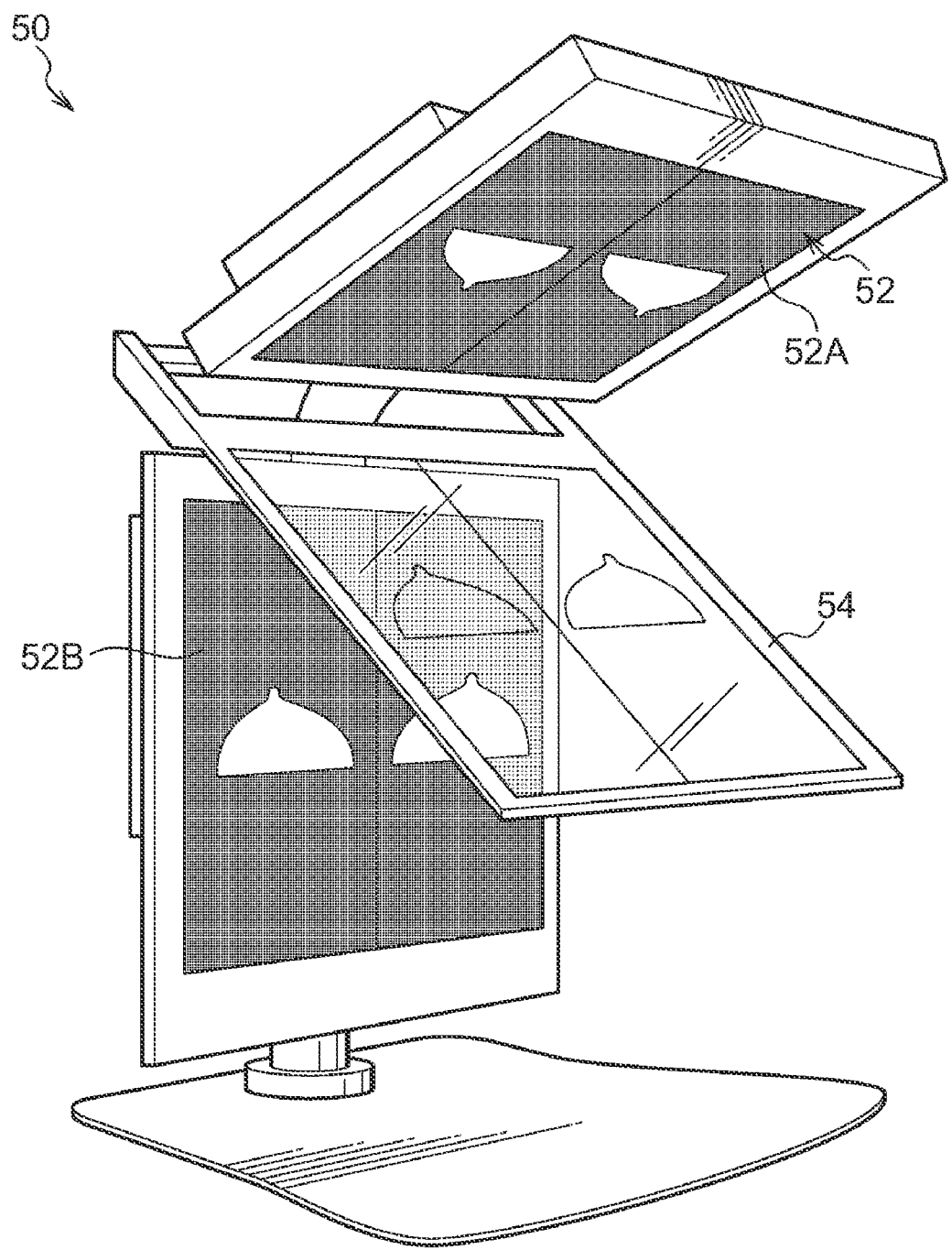
FIG. 4 is a schematic perspective view of an image display device relating to the exemplary embodiment.
Figure 5:
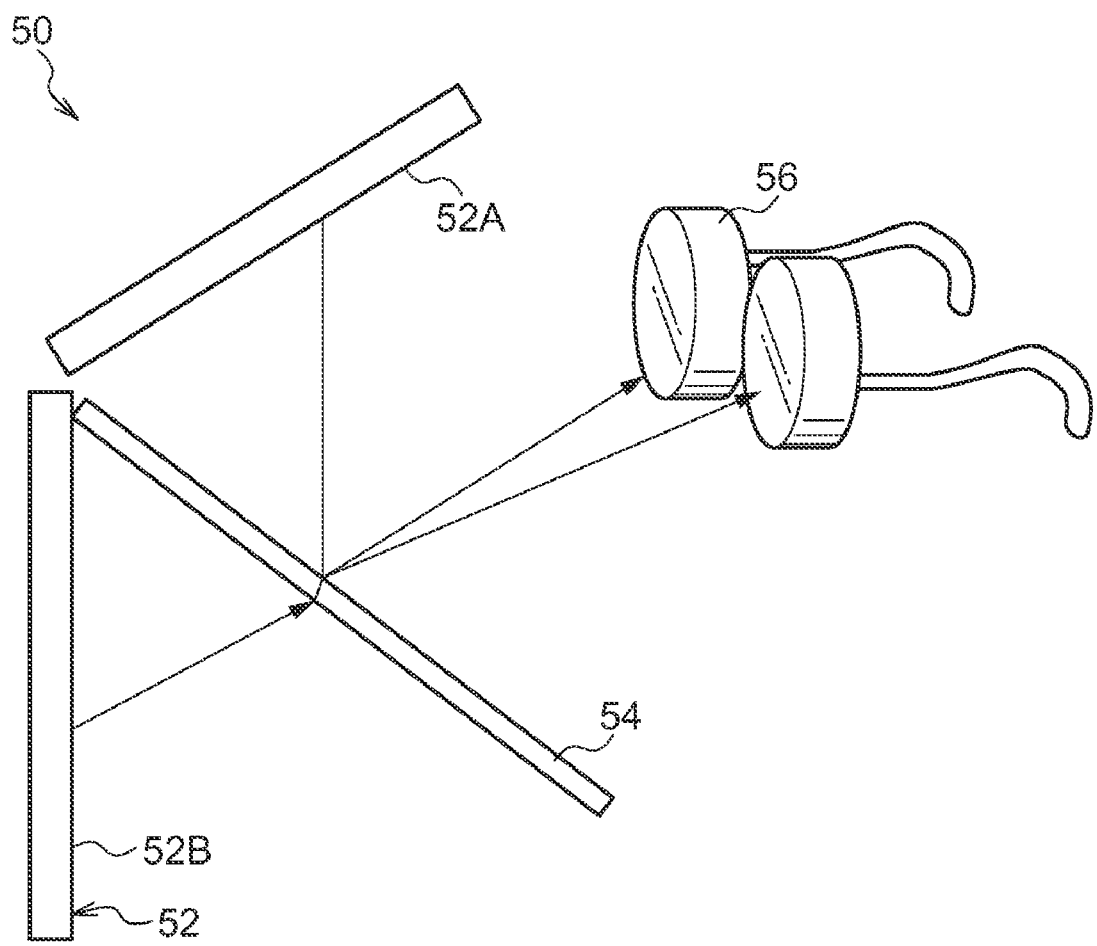
FIG. 5 is a schematic side view of the image display device relating to the exemplary embodiment.

As shown in FIG. 4 and FIG. 5, an image display device 50 relating to the present exemplary embodiment has a display screen 52 for displaying the images, and a beam splitter mirror (polarizing plate) 54. The display screen 52 is structured by an upper screen 52A that is disposed at the upper portion side, and a lower screen 52B that is disposed at the lower portion side.

For example, if the dominant eye of the radiologist is the right eye, the image captured by the radiation source 24 that was at the directly-facing position C is displayed on the upper screen 52A. The image displayed on the upper screen 52A is reflected at the beam splitter mirror (polarizing plate) 54, and is visually recognized by the right eye of the radiologist who is wearing passive polarizing glasses 56.

The image captured by the radiation source 24 that was at the first diagonal incidence position S1 is displayed on the lower screen 52B. The image displayed on the lower screen 52B is transmitted through the beam splitter mirror (polarizing plate) 54, and is visually recognized by the left eye of the radiologist who is wearing the passive polarizing glasses 56. Due thereto, the image from the directly-facing position C is visually confirmed by the dominant eye, and it is easy for the radiologist to stereoscopically view the images.

The present invention is not limited to mammography and the above-described exemplary embodiment, and various modifications, changes and improvements can be made thereto.

What is claimed is:

1. A radiographic imaging device comprising:
a radiation source that irradiates radiation onto an object of imaging, and that can move to a directly-facing position at which the radiation source directly faces the object of imaging in a directly-facing direction, a first diagonal incidence position that is at an angle with respect to the directly-facing position, and a second diagonal incidence position that is at an angle at a side opposite the first diagonal incidence position with respect to the directly-facing position;
a radiation detector that detects radiation that is irradiated from the radiation source and transmitted through the object of imaging, a radiographic image being generated from the detected radiation; and
a control section that acquires radiologist information relating to a radiologist, and that, based on the acquired radiologist information, selects one of the first diagonal incidence position or the second diagonal incidence position,
wherein the acquired radiologist information includes at least one of dominant eye information indicating a dominant eye of the radiologist or information indicating a visual acuity of the radiologist, and
wherein the radiographic imaging device captures radiographic images at the directly-facing position and at the selected one of the first diagonal incidence position or the second diagonal incidence position selected by the control section.

2. The radiographic imaging device of claim 1, wherein, when the dominant eye information indicates a right eye, the control section is configured to select a particular one of the first diagonal incidence position or the second diagonal incidence position, and, when the dominant eye information indicates a left eye, the control section is configured to select another of the first diagonal incidence position or the second diagonal incidence position.

3. The radiographic imaging device of claim 1, wherein the radiation source is configured to irradiate a radiation dose the object of imaging that is smaller at each of the first diagonal incidence position and the second diagonal incidence position than at the directly-facing position.

4. The radiographic imaging device of claim 2, wherein the radiation source is configured to irradiate a radiation dose onto the object of imaging that is smaller at each of the first diagonal incidence position and the second diagonal incidence position than at the directly-facing position.

* * * * *